United States Patent
Pugh

[11] Patent Number: 5,846,486
[45] Date of Patent: Dec. 8, 1998

[54] HOLLOW FRUSTUM REAGENT TEST DEVICE

[75] Inventor: Jerry Thomas Pugh, Mountain View, Calif.

[73] Assignee: Lifescan, Inc., Milpitas, Calif.

[21] Appl. No.: 694,960

[22] Filed: Aug. 9, 1996

[51] Int. Cl.⁶ .................................................. G01N 21/78
[52] U.S. Cl. ............................................ 422/56; 422/58
[58] Field of Search ................... 422/55, 56, 57, 422/58, 99, 100, 101, 82.05

[56] References Cited

U.S. PATENT DOCUMENTS

| | | | |
|---|---|---|---|
| 3,991,617 | 11/1976 | d'Autry | 73/425.4 P |
| 3,992,158 | 11/1976 | Przybylowicz et al. | 422/57 |
| 4,774,058 | 9/1988 | Mehl | 422/101 |
| 4,787,398 | 11/1988 | Garcia et al. | 128/770 |
| 4,952,373 | 8/1990 | Sugarman et al. | 422/99 |
| 5,100,620 | 3/1992 | Brenneman | 422/58 |
| 5,137,691 | 8/1992 | Parker | 422/58 |
| 5,304,468 | 4/1994 | Phillips et al. | 435/14 |
| 5,556,598 | 9/1996 | Raybuck et al. | 422/100 |
| 5,563,031 | 10/1996 | Yu | 435/4 |

FOREIGN PATENT DOCUMENTS 0588564  3/1994  European Pat. Off. .

*Primary Examiner*—Jeffrey Snay
*Attorney, Agent, or Firm*—James Riesenfeld

[57] ABSTRACT

A hollow, frustum-shaped disposable device is used in an apparatus for measuring the concentration of an analyte in a sample of a biological fluid. The smaller end of the frustum has a porous membrane, to which a sample of the fluid may be applied. Preferably, a reagent in the membrane reacts with the analyte to cause a color change. The device is mounted on a meter, which measures the color change and computes from the change the analyte concentration in the sample. The apparatus permits remote dosing of the device, which minimizes the likelihood of cross-contamination between the user and the meter. Devices can be mounted on the meter and released from the meter without touching them, to further protect against contamination.

8 Claims, 10 Drawing Sheets

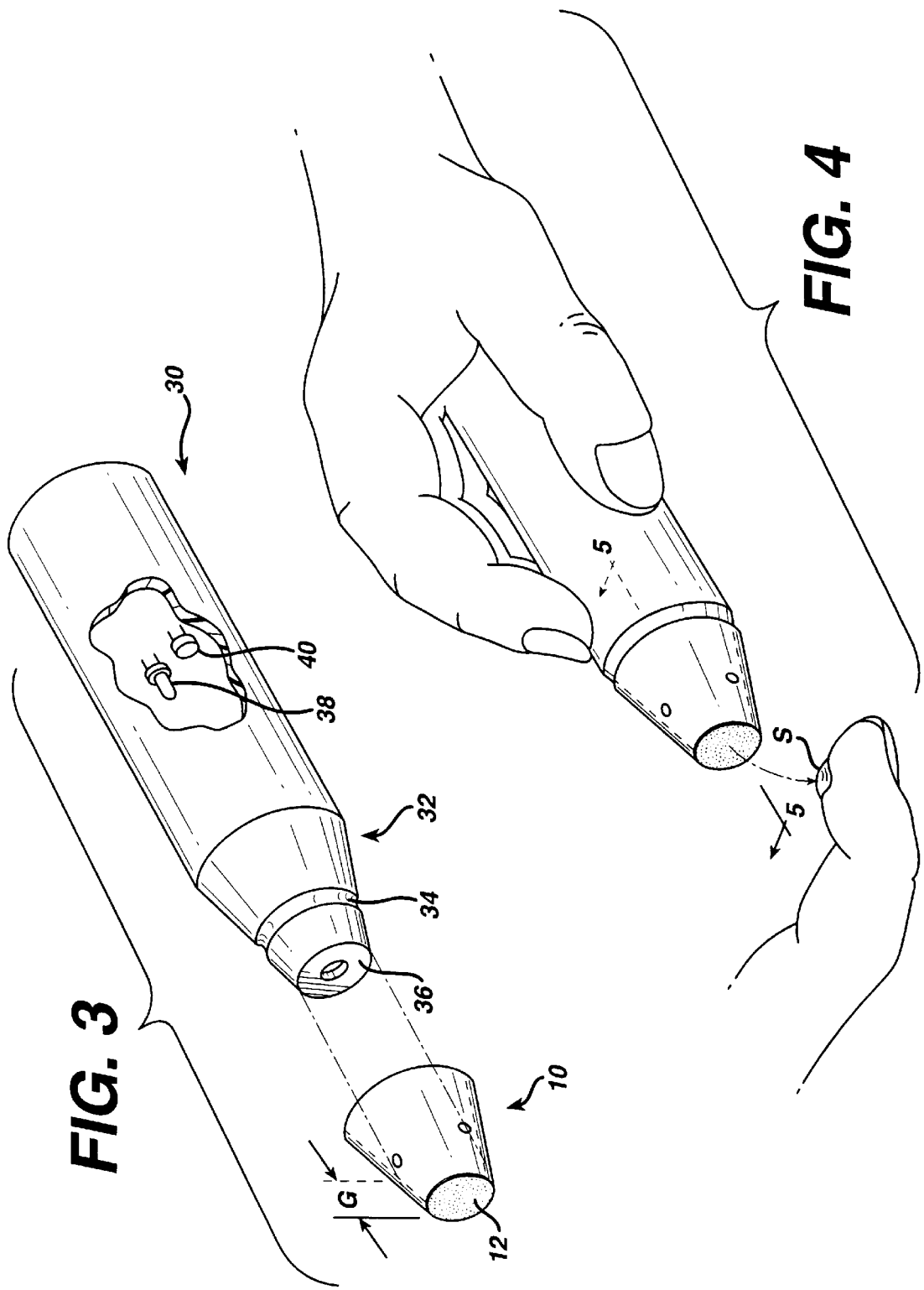

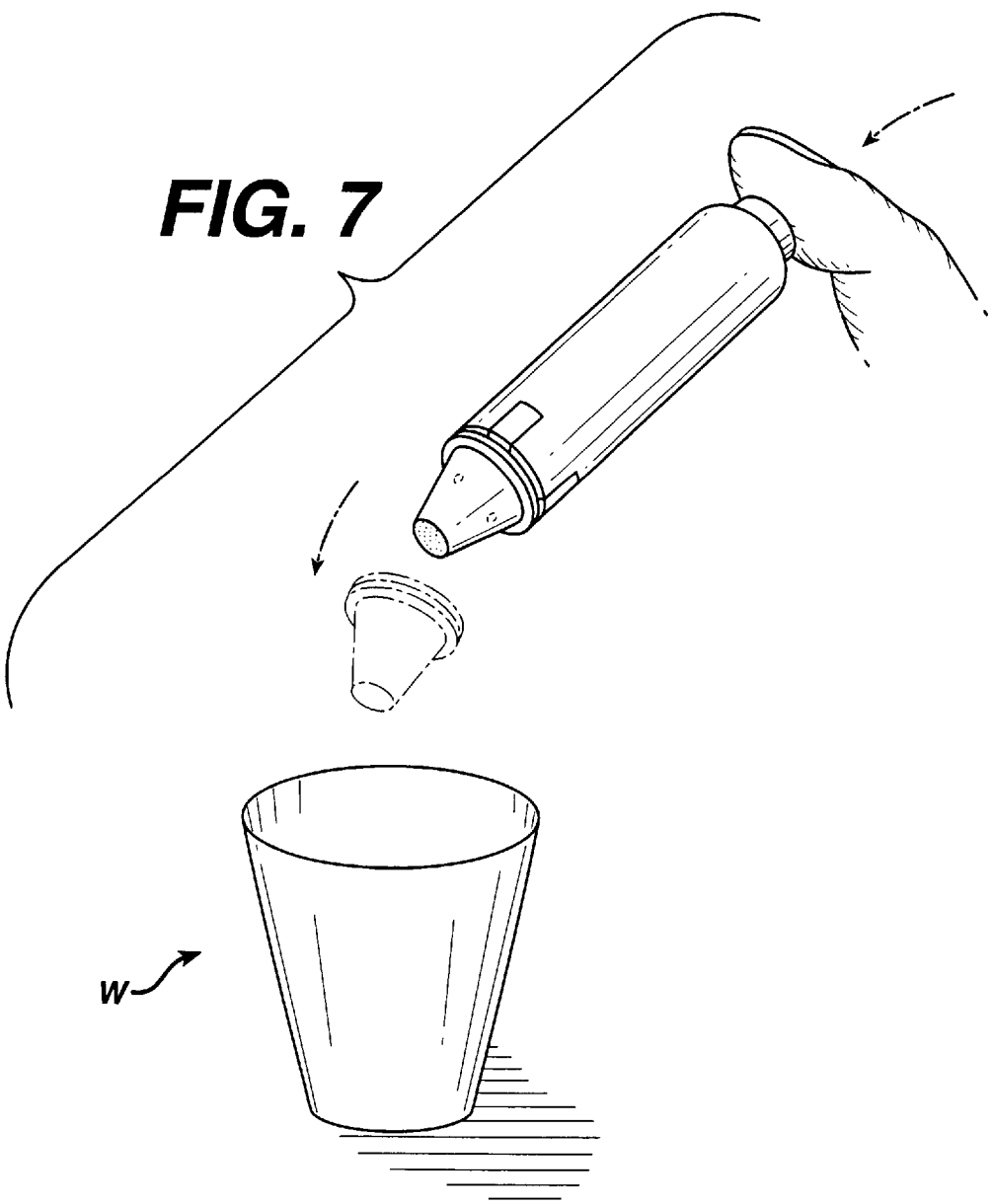

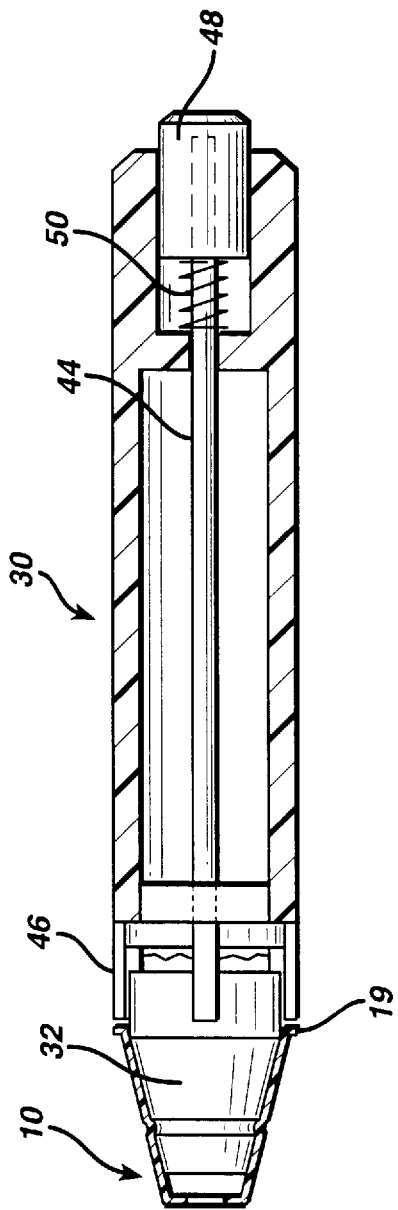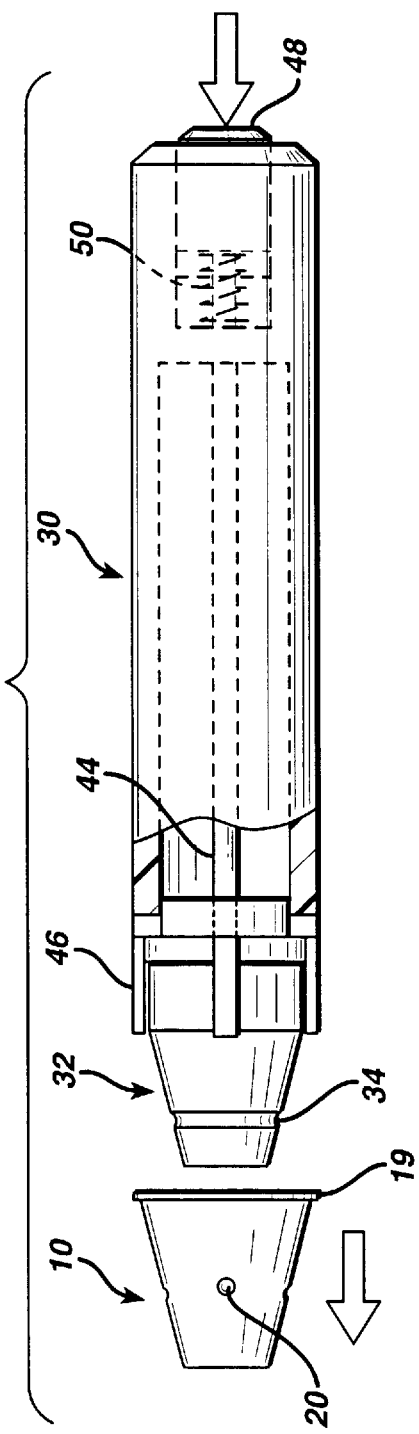

HOLLOW FRUSTUM REAGENT TEST DEVICE

BACKGROUND OF THE INVENTION

1. Field of the Invention

This invention relates to a meter and disposable device for measuring the concentration of an analyte in a biological fluid; more particularly, an apparatus for which the disposable device is a hollow frustum.

2. Description of the Related Art

Medical diagnosis often involves measurements on biological fluids, such as blood, urine, or saliva, that are taken from a patient. Generally, it is important to avoid both contamination of equipment and personnel with these fluids and to avoid contamination of the patient with fluids from others. Thus, there is a need for diagnostic devices that minimize the risk of such contamination.

Among the medical diagnostic devices that are in most widespread use today is the blood glucose monitor. In the U.S. alone, there are an estimated 14 million people with diabetes. In order to avoid serious medical problems, such as vision loss, circulatory problems, kidney failure, etc., many of these people monitor their blood glucose on a regular basis and then take the steps necessary to maintain their glucose concentration in an acceptable range.

Blood contamination is of concern when making a blood glucose measurement. For example, when using the most common types of whole blood glucose meters (photometric), the glucose determination is generally made from a blood sample that is applied to a test strip that is on the meter. To apply the patient's finger-stick blood sample, the patient's finger must be positioned above and near to the test strip in order to inoculate the test strip with the blood sample. There is a risk that the patient's finger may come into contact with a portion of the meter that is contaminated with blood from previous use by others, particularly when used in a hospital.

This risk to the patient is minimized if the test strip is inoculated before it is placed into the meter. This is the so called "off-meter dosing" approach. With this approach, the patient applies his blood sample to a reagent test strip as the first step in the measurement process. Then the strip is inserted into the meter. The patient's finger only comes into contact with a new (clean) disposable, which cannot be contaminated by another patient's blood. The finger never comes into contact with a contaminated portion of the meter. The approach of off-meter dosing has been used for some time, particularly with meters that operate photometrically, as well as in systems that measure hematocrit. A disadvantage of off-meter dosing is that the meter cannot take a measurement at or before "time-zero", the time when the sample was applied to the strip. In a photometric meter, a reflectance reading prior to strip inoculation permits the meter to correct for variations in strip background color and positioning. The meter can also determine time-zero more directly and more accurately, which facilitates accurate measurements. By contrast, time-zero may be difficult or impossible to determine if the strip is inoculated off-meter.

Although off-meter dosing reduces the contamination problem for the patient, the meter can still become contaminated with blood. There is thus a risk to others who may come into contact with the contaminated meter, such as workers in a hospital and meter repair technicians. Furthermore, if the patient is being assisted by a healthcare worker, that worker could come into contact with the patient's blood while removing the strip for disposal, after the test has been completed.

Meters that operate electrochemically typically use "remote dosing", in which the test strip is placed in the meter before inoculation, but the blood application point is remote from the meter surfaces that can become contaminated. For example, the Glucometer Elite® from Bayer Diagnostics and the Advantage® from Boehringer Maruheim incorporate electrodes with remote sample application. As with off-meter dosing, strip removal may also pose a risk for meters that use remote dosing.

A number of systems have been disclosed that are aimed at reducing the risk of contamination to a patient and/or to others in connection with diagnostic tests.

U.S. Pat. No. 4,952,373, issued Aug. 28, 1990, to Sugarman et al., discloses a shield that is designed to prevent excess liquid on diagnostic cartridges from being transferred to a monitor with which the cartridge is used. The shield is fabricated from thin plastic or metallic film and is attached to a cartridge that is generally the size of a credit card.

U.S. Pat. No. 5,100,620, issued Mar. 31, 1992, to Brenneman, discloses an inverse funnel shaped body with a central capillary tube to transport a liquid sample from a remote sample-application point to a test surface. The device can be used to transfer blood from a finger stick to a reagent film.

U.S. Pat. No. 3,991,617, issued Nov. 16, 1976, to Marteau d'Autry discloses a device that is used with a pipette intended to be used with disposable tips. The device provides a push button mechanism for ejecting the tip from the end of the pipette.

The common element of the above patents is that each of the devices disclosed addresses the risk of contamination that is posed by biological fluids and other potentially hazardous liquids.

SUMMARY OF THE INVENTION

In accordance with the present invention, a device for use in an apparatus for measuring a concentration of an analyte in a sample of a biological fluid comprises (a) a hollow frustum, having open ends of unequal size and (b) a porous membrane for accepting the sample, attached to, and substantially closing, the smaller open end, the membrane comprising
  (i) a surface for accepting the sample and
  (ii) a reagent for reacting with the analyte to cause, in a physically detectable parameter of the membrane, a change that can be measured and be related to the concentration of the analyte in the sample.

A method of this invention for measuring a concentration of an analyte in a sample of a biological fluid comprises (a) providing a device that comprises a hollow frustum having open ends of unequal size, whose smaller end is substantially closed by a membrane that has
  (i) a surface for accepting the sample and
  (ii) a reagent for reacting with the analyte to cause, in a physically detectable parameter of the membrane, a change that can be measured and be related to the concentration of the analyte in the sample;

(b) applying the sample to the membrane surface;

(c) measuring the change in the parameter; and (d) determining the analyte concentration from the measurement of the parameter change.

The device of the present invention can be used advantageously with a meter for measuring a concentration of an analyte in a sample of biological fluid that is applied to a first surface of a porous membrane that contains a reagent, which reacts with the analyte to cause a change in reflectance of a second surface of the membrane, the membrane being attached to and substantially closing an end of a hollow frustum device. The meter comprises (a) a body having a frustum-shaped distal section for mating engagement with the device, the section tapering inwardly to an end that faces the second surface of the membrane, (b) an optical system in the body to direct a beam of light out from the distal end and to accept light reflected back from the second surface of the membrane, (c) means for measuring the light reflected back into the body both before and after the sample is applied to the membrane, and (d) means for computing the analyte concentration in the fluid from the measured values of reflected light.

The device of the present invention permits a person to measure the analyte concentration in a biological fluid, while minimizing the risk that the fluid or the user will come into contact with the measurement apparatus. Thus, the device reduces both the likelihood of contamination of the apparatus by the user and vice versa. The device is disposable, and the terms "device" and "disposable" are used interchangeably throughout this specification and the appended claims.

BRIEF DESCRIPTION OF THE DRAWINGS

FIG. 3 is a perspective view of a meter and device of the invention prior to their being attached;

FIG. 4 is a perspective view of the meter and device in the process of obtaining a blood sample;

FIG. 7 is a perspective view of a meter of this invention ejecting a device;

FIG. 8 is a longitudinal cross section, with certain parts in elevation for clarity, of the meter of FIG. 7 in a first, in-use, position;

FIG. 9 is a side elevational view, partially in cross section, of the meter of FIG. 7 in a second, ejection, position;

DETAILED DESCRIPTION OF THE INVENTION

The device of the present invention is generally adapted for use in an apparatus for measuring the concentration of analytes, such as alcohol, cholesterol, proteins, ketones, enzymes, phenylalanine, and glucose, in biological fluids such as blood, urine, and saliva. For brevity, we describe the details for using the device in connection with self-monitoring of blood glucose; however, a person of ordinary skill in the art of medical diagnostics would be able to readily adapt the technology for measuring other analytes in other biological fluids.

Self-monitoring of blood glucose is generally done with meters that operate on one of two principles. The first is the photometric type, which is based on reagent strips that include a composition that changes color after blood is applied. The color change is a measure of the glucose concentration.

The second type of blood glucose monitor is electrochemical and operates on the understanding that blood applied to an electrochemical cell can cause an electrical signal—voltage, current, or charge, depending on the type of meter—that can be related to the blood glucose concentration.

The present invention permits convenient, remote dosing for both photometric and electrochemical systems. For brevity, the description below focuses on a photometric system. Similar devices can be used with an electrochemical system. With either type of system, the present device permits the meter to monitor the complete course of the reaction, from the time the sample is applied until a glucose determination is made. The ability to measure the test start time makes it easier to determine the glucose concentration accurately.

There are some advantages to using a photometric rather than an electrochemical system to make a glucose determination. One advantage of a photometric system is that measurements can be made at more than one wavelength of light, and corrections can be made for variations in blood hematocrit. The disposable disclosed here provides these advantages of the photometric system, while also permitting minimal meter contamination.

The disposables used in photometric measurement systems are generally made in the form of a thin rectangular strip. The shape derives from the original so-called "dip and read" test strip configuration. One end serves as a handle, while the chemical reaction with the fluid sample is carried out at the other end.

These rectangular disposables form the male portion of the interface with the meter. That is, the strip is retained by features on the meter that enclose the disposable. This method of retention invites contamination of the meter with the fluid sample.

In order to avoid the problems of contamination the present disposable takes the form of a hollow frustum, which provides the female portion of the interface with the meter. That is, the disposable encloses a portion of the meter and serves as a cover to prevent contamination of the meter by the fluid sample.

Figure 1:
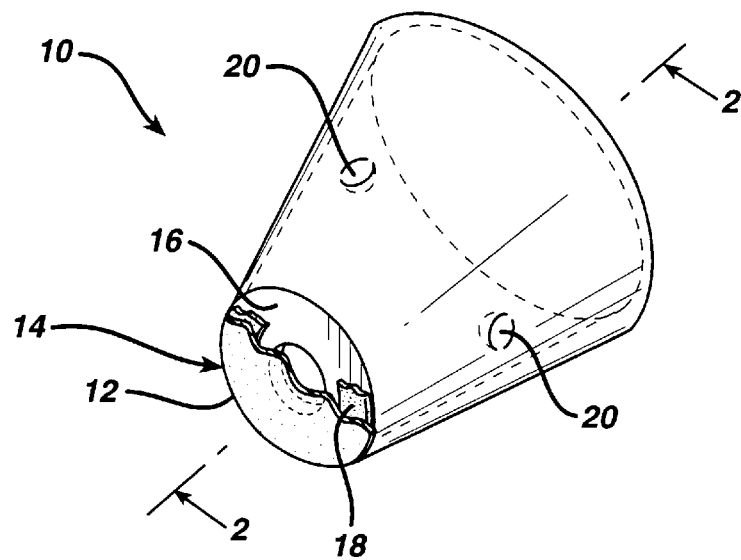
FIG. 1 is a perspective view of a device of this invention with a portion broken away for clarity.

FIG. 1 depicts in partial cutaway an embodiment of this invention in which the disposable 10 is a hollow frustum of a cone. Membrane 12 is attached to the smaller end 14. Optional lip 16 provides a surface to which membrane 12 is attached with adhesive 18. Optional indentations 20 are spaced around the circumference of the cone to provide a retention mechanism, in conjunction with a groove on a meter.

Figure 2:
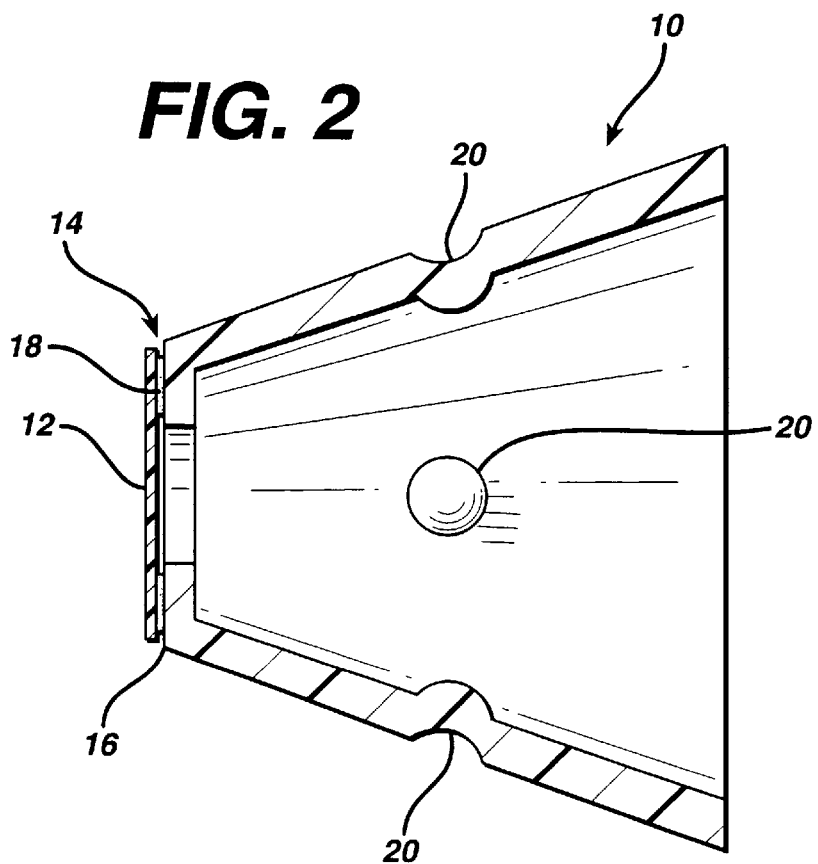
FIG. 2 is a cross-sectional view taken along line 2—2 of FIG. 1.
Figure 11:
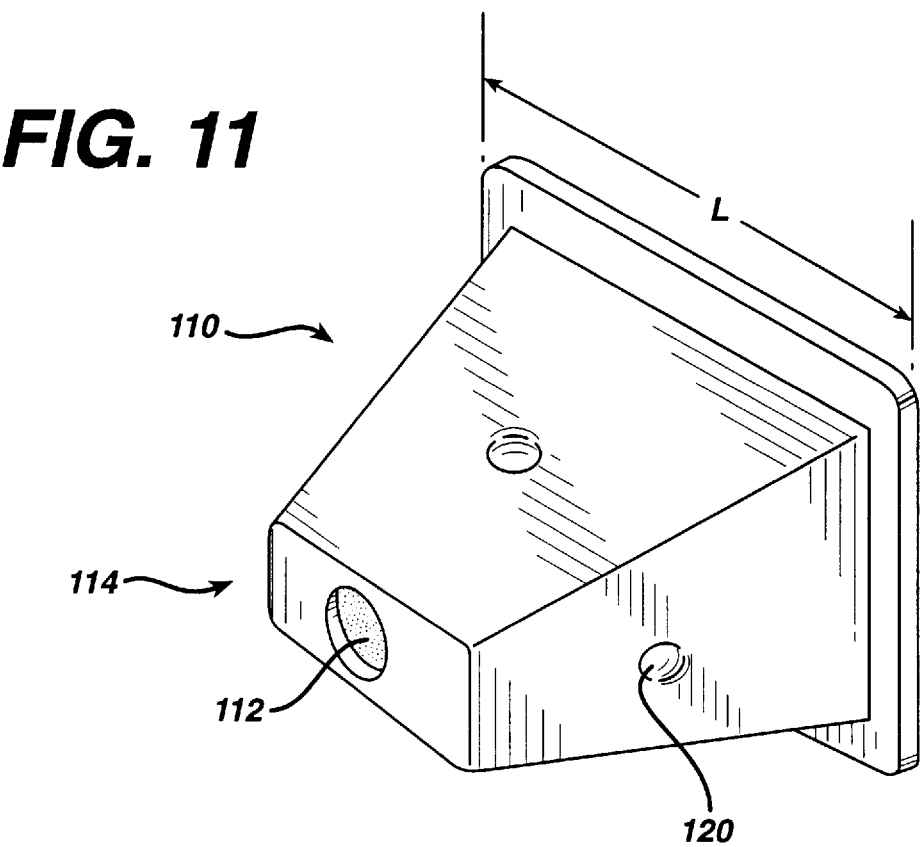
FIG. 11 is a perspective view of an alternate embodiment of a device of this invention.

FIG. 2 is a cross section of the disposable of FIG. 1 taken along the line 2—2. As shown in FIG. 2, the membrane is attached to the outside of the disposable. Alternatively, as shown in FIG. 11, the membrane may be attached to the inside of the disposable.

FIG. 3 is an exploded perspective view of a photometric meter and a disposable device of the type shown in FIG. 1. Meter 30 has an elongated configuration with a distal section 32 that is a substantially cylindrically symmetrical frustum, along whose perimeter is optionally a groove 34. Note that the disposable nests on the distal section of the meter in such a way that there is an accurately defined gap G between the distal end 36 of meter 30 and the bottom surface of membrane 12. The accurate positioning contributes to measurement precision and reliability. In the cutout can be seen a light source 38 and detector 40, which provide for illuminating a disposable and for detecting light reflected from the disposable, respectively. As discussed below, measuring light reflected from the disposable yields the glucose concentration in the sample applied to the membrane. Although only one source and detector are shown in FIG. 3, multiple sources, optionally having different output spectra, and/or multiple detectors may be used.

FIG. 4 is a perspective view of the way in which a device and meter of FIG. 3 can be used to obtain a sample S from a stuck finger tip. It is quite easy for the user to bring the disposable into contact with the finger, which is a big advantage for users that have impaired vision.

Figure 5:
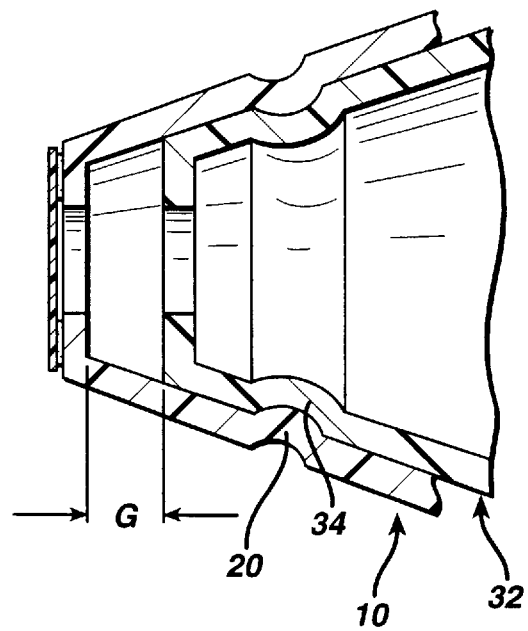
FIG. 5 is a partial cross-sectional view of the meter and device of FIG. 4, taken along line 5—5 of FIG. 4.

FIG. 5 is a cross section of part of distal section 32 of meter 30 and disposable 10, which illustrates the way indentations 20 and groove 34 positively locate meter 30 within disposable 10, leaving gap G. Note that gap G ensures that blood that penetrates through the membrane does not contaminate the meter. The gap dimension, while not critical, is preferably at least about ½ mm.

Figure 6:
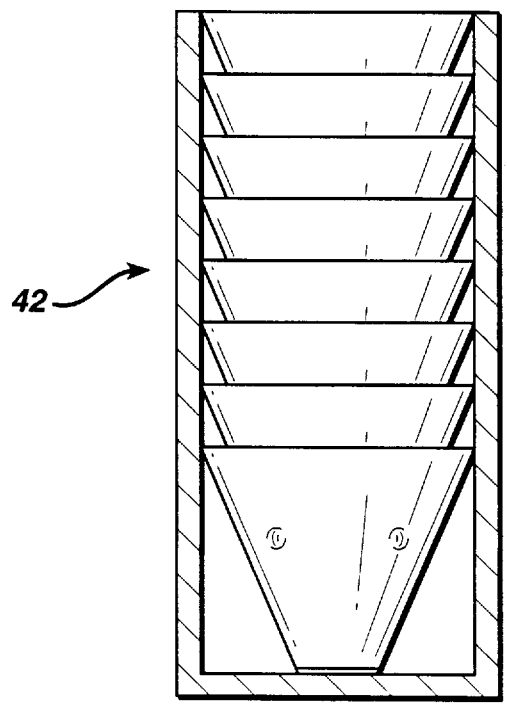
FIG. 6 is a side view in partial cross section of a plurality of devices in a package.

An advantage of the device of the invention, when used with a meter of the type shown in FIG. 3, is that the devices can be in a stack, nested conveniently in a container 42, as shown in FIG. 6. A device can then be secured simply by inserting the distal section 32 of meter 30 into container 42 and engaging groove 34 and indentations 20. After a test has been completed, a used disposable can be ejected into waste container W, as shown in FIG. 7, provided there is an optional push-button ejection mechanism.

Push-button ejection mechanisms of the type that are widely known and used are suitable for this invention (see e.g.; U.S. Pat. No. 3,991,617). One such mechanism is depicted in FIGS. 8 and 9, which show a push-button mechanism mounted in a meter of the type shown in FIG. 3. The elements of the mechanism include shaft 44, which joins ejector 46 and push button 48. Push button 48 works through shaft 44 to cause ejector 46 to disengage disposable 10 from the distal section 32 of meter 30. Spring 50 works to return the ejector 46 and push button 48 to their retracted position. Push-button ejection, by permitting the disposable to be removed without direct contact, helps to avoid contamination. Disposables to be used with push-button ejection mechanisms of the type shown in FIGS. 8 and 9 preferably have a flange 19.

Figure 10:
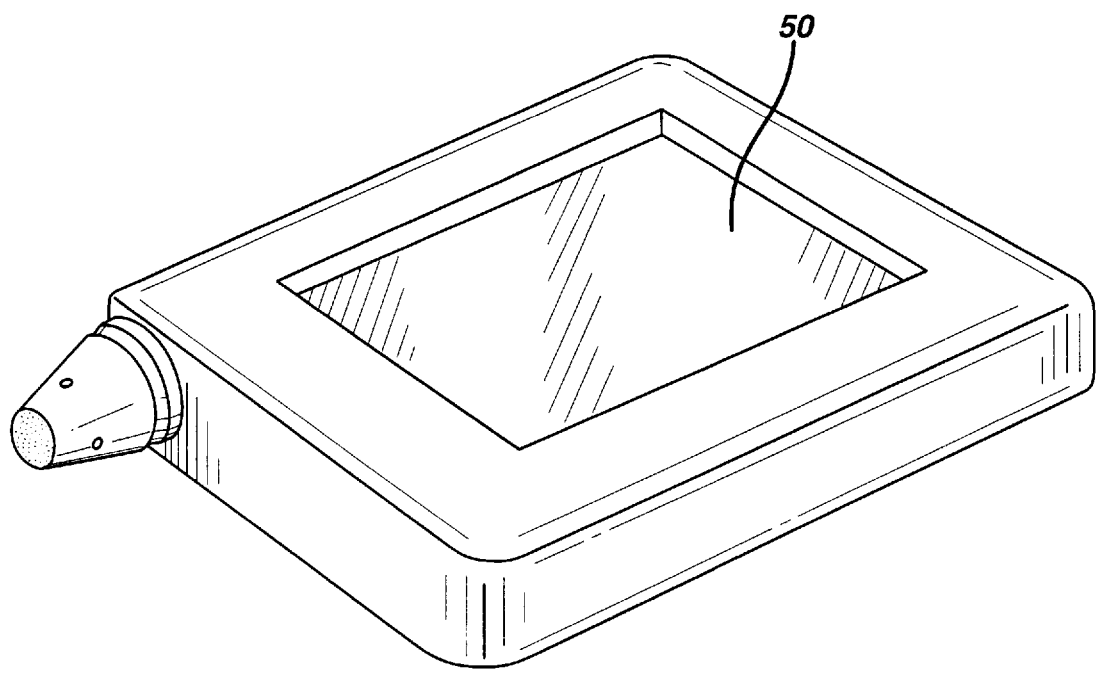
FIG. 10 is a perspective view of an alternate embodiment of a meter.

FIG. 10 depicts an embodiment of a meter of this invention, which includes a display 50 for depicting the analyte concentration measured by the meter. The display can be a light-emitting diode (LED) display, a liquid crystal display (LCD), or similar display well known in the art.

Although the above description and Figs. contemplate a disposable having a circular cross section and meter having a distal section having a mating cross section, that geometry is not essential and, in fact, may not even be preferred. A primary consideration in selecting the geometry in a photometric system is the optical design. Generally, reflectometry dictates at least a minimum angular separation (typically 45°) between a detector and specularly reflected light. This, in turn requires at least a minimum vertex angle of the conical disposable. However, it is an advantage to a user to be able to view his/her finger for dosing, and a large vertex angle interferes with that view. Thus, a disposable having a rectangular cross section may be preferred, such as the hollow frustum of a rectangular pyramid 110 shown in FIG. 11. In that case, the angular separation between detector and specular-reflected light determines only the minimum feasible value of L, the longitudinal dimension of the larger open end. But the disposable could be smaller and provide less interference with a user's view of his/her finger. Furthermore, rectangular membranes can be fabricated from ribbons or sheets at less expense and with less waste of material. Nevertheless, a circular cross section is advantageous when an array of several sources and/or detectors is used in the optical system.

Figure 12:
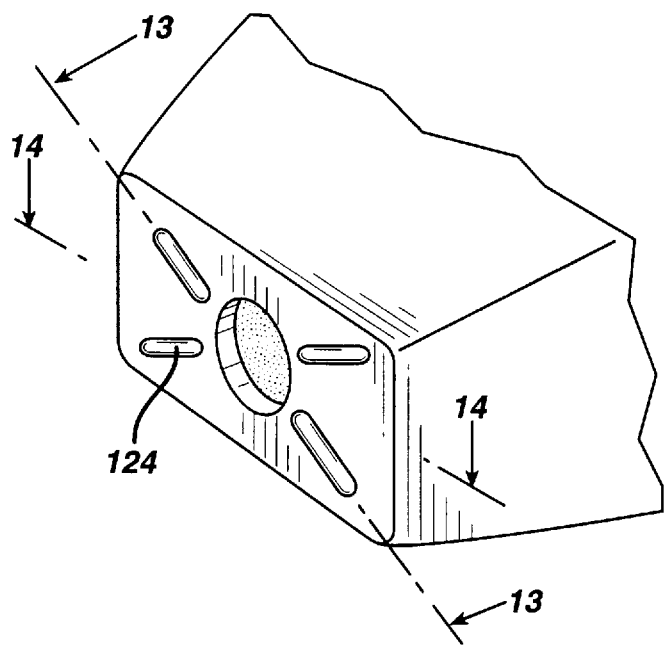
FIG. 12 is a fragmentary perspective view of the distal end of the device of FIG. 11.
Figure 13:
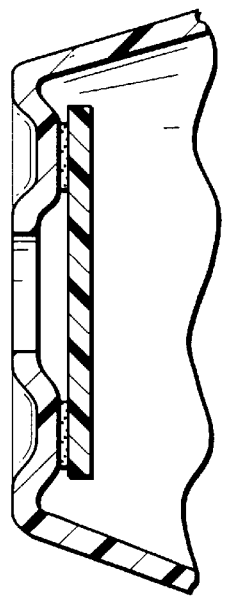
FIG. 13 is a cross-sectional view taken along line 13—13 of FIG. 12.
Figure 14:
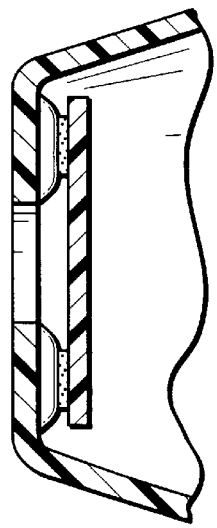
FIG. 14 is a cross-sectional view taken along line 14—14 of FIG. 12.
Figure 15:
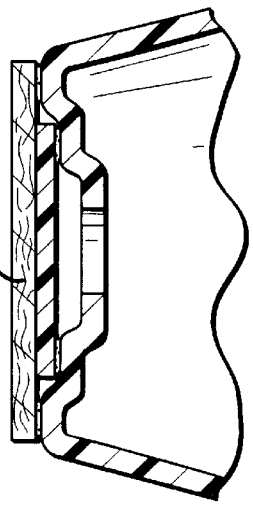
FIG. 15 is a cross-sectional view of a further embodiment of the distal end of a device of the invention.

Since contamination is possible if excess sample were to drop from the disposable, it is desirable to accommodate large samples, without dripping. Various designs can serve to retain excess sample. One is shown in FIGS. 12,13, and 14. FIG. 12 depicts the disposable of FIG. 11 with indentations 124 on the small-end surface of the disposable. As shown in FIGS. 13 and 14, the indentations allow capillary flow to fill the resulting gap between the membrane and the top inside surface of the device. An alternative way of forming such gaps is to adhere the membrane to the disposable with thick adhesive, leaving gaps to accommodate the excess sample. Another way to absorb excess sample is to attach an absorbent pad 126 over the front surface of the membrane, as shown in FIG. 15.

Figure 16:
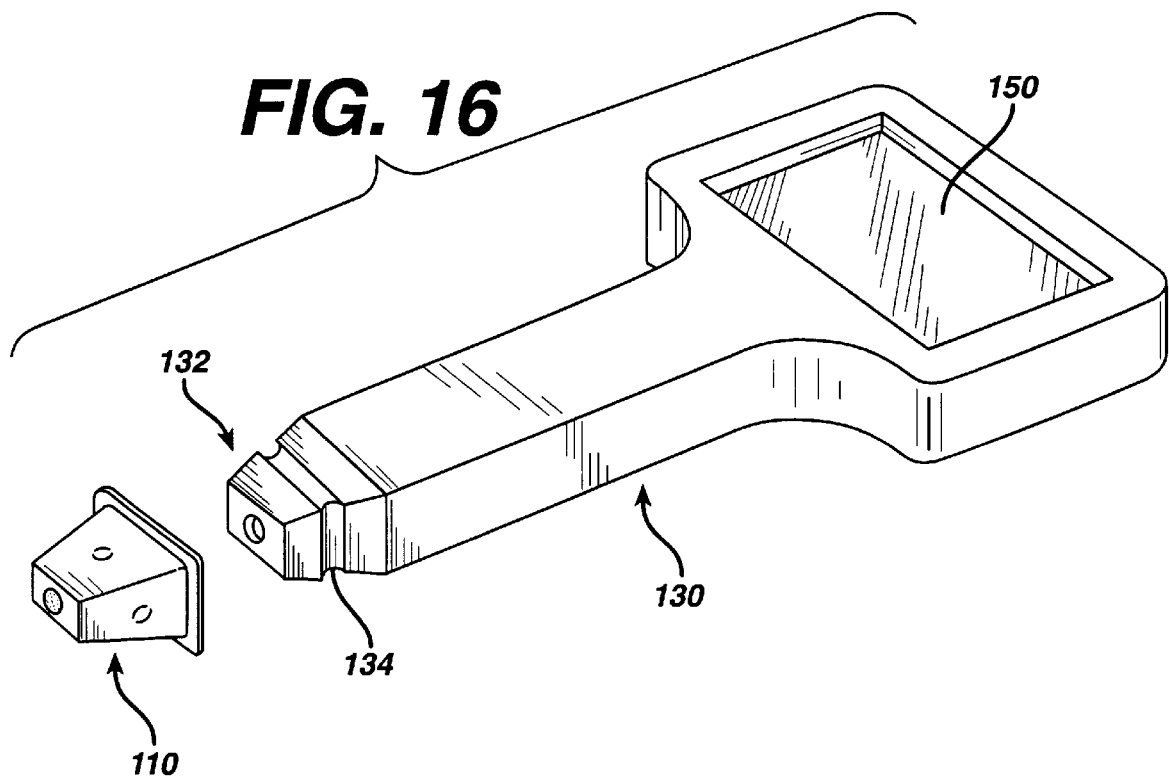
FIG. 16 is a perspective view of another embodiment of a meter and device prior to their being attached.

FIG. 16 is an exploded perspective view of a meter and a disposable of the type shown in FIG. 11. The distal section 132 of meter 130 has an optional groove 134, which is similar to groove 34, for retaining the disposable. Elongated neck 130 facilitates pickup of disposables from the elongated containers 42 shown in FIG. 6. Display 150 depicts the measured analyte concentration.

Figure 17:
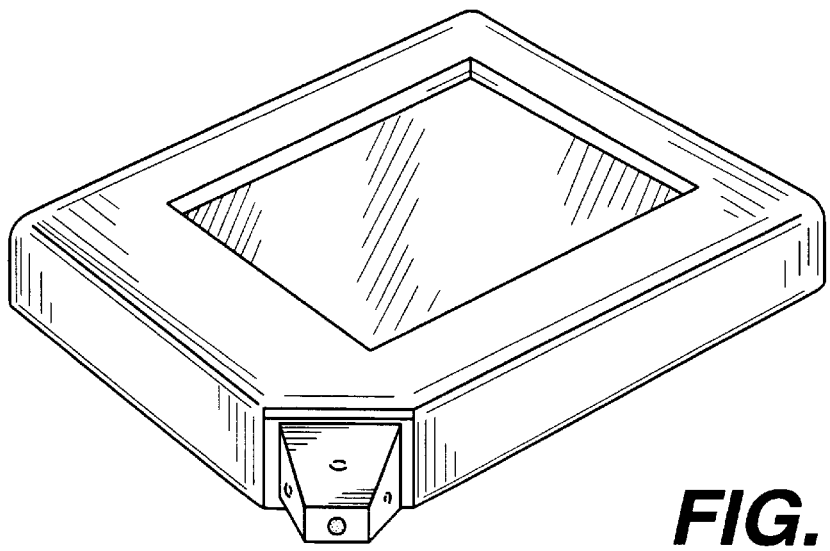
FIG. 17 is another embodiment of a meter and device.

FIG. 17 depicts an alternative embodiment of a meter adapted for use with the disposable of FIG. 11.

Figure 18:
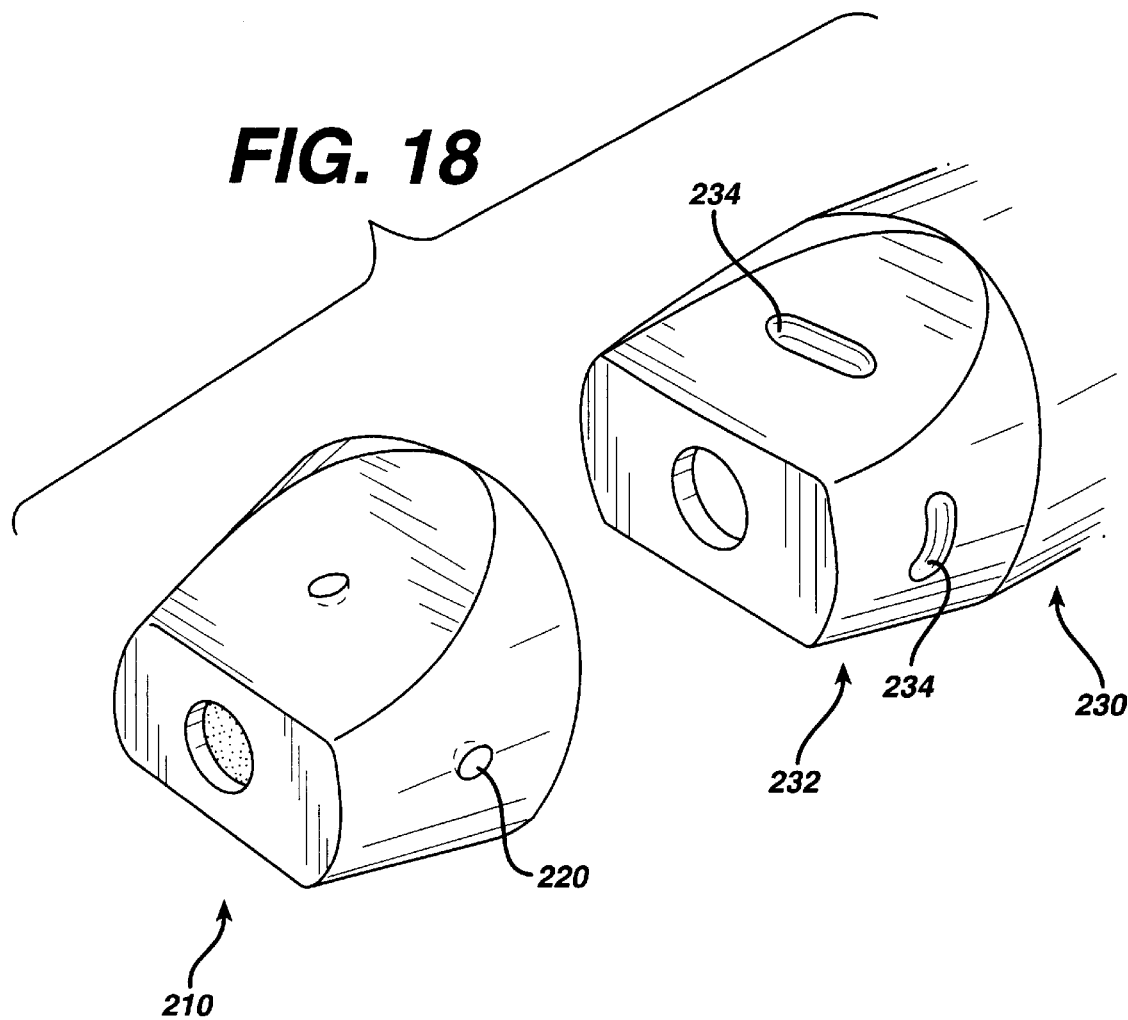
FIG. 18 is a perspective view of the distal end of a further embodiment of the meter and device.

FIG. 18 depicts the distal portion of yet another embodiment of a disposable 210 and meter 230. Distal section 232 mates with disposable 210. Note that slots 234 are an alternative to groove 34 (or 134) for capturing indentations, such as 220, on the disposable.

Figure 19:
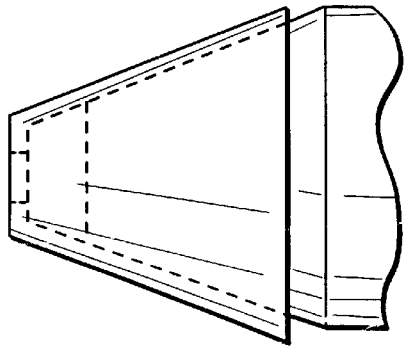
FIG. 19 is a side view of the distal end of the meter and device of FIG. 18 shown in an assembled position.

FIG. 19 is a side view of the embodiment of FIG. 18.

In the method of this invention, a blood sample is picked up on the outward-facing surface of the membrane. Glucose in the sample interacts with a reagent in the membrane to cause a color change, which changes the reflectance of the inward-facing membrane surface. The light source in the meter illuminates the inward-facing membrane surface and measures the intensity of light reflected from that surface. Using the appropriate computation, the change in reflectance yields the glucose concentration in the sample.

A variety of combinations of membrane and reagent compositions are known for photometric determinations of blood glucose concentration. A preferred membrane/reagent composition is a polyamide matrix incorporating an oxidase enzyme, a peroxidase, and a dye or dye couple. The oxidase enzyme is preferably glucose oxidase. The peroxidase is preferably horseradish peroxidase. A preferred dye couple is 3-methyl-2 benzothiazolinone hydrazone hydrochloride plus 3,3-dimethylaminobenzoic acid. Details of that membrane/reagent combination and variations on it appear in U.S. Pat. No. 5,304,468, issued Apr. 19, 1994, to Phillips et al., incorporated herein by reference.

Another preferred membrane/reagent composition is an anisotropic polysulfone membrane (available from Memtec America Corp., Timonium, Md.) incorporating glucose oxidase, horseradish peroxidase, and the dye couple [3-methyl-2-benzothiazolinone hydrazone] N-sulfonyl benzenesulfonate monosodium combined with 8-anilino-1-naphthalene sulfonic acid ammonium. Details of that membrane/reagent combination and variations on it appear in U.S. patent application Ser. No. 08/302,575, filed Sep. 8, 1994, incorporated herein by reference.

It will be understood by those skilled in the art that the foregoing descriptions of embodiments of this invention are illustrative of practicing the present invention but are in no way limiting. Variations of the detail presented herein may be made without departing from the scope and spirit of the present invention.

I claim:

1. A device for use in an apparatus for measuring a concentration of an analyte in a sample of a biological fluid, comprising (a) a hollow frustum, having open ends of unequal size, the smaller open end having an inward-extending lip, and (b) a porous membrane for accepting the sample, attached to raised portions of a surface of the lip and substantially closing the smaller open end, the membrane comprising
   (i) a first surface for accepting the sample and
   (ii) a reagent for reacting with the analyte to cause a color change at a second surface, opposite to the first surface, resulting in a change in reflectance at the second surface that can be measured and be related to the concentration of the analyte in the sample.

2. The device of claim 1, in which the frustum has a rectangular cross section.

3. The device of claim 1 in which the frustum has a circular cross section.

4. The device of claim 1 in which the membrane comprises polyamide.

5. The device of claim 1 in which the membrane comprises polysulfone.

6. The device of claim 1 in which the frustum has a plurality of circumferential indentations.

7. The device of claim 1 further comprising an absorbent pad over the first surface of the membrane.

8. The device of claim 1 in which the larger open end has an outward-extending flange.

* * * * *